(12) United States Patent
Hansen et al.

(10) Patent No.: US 6,603,318 B2
(45) Date of Patent: Aug. 5, 2003

(54) METHOD OF DETERMINING WHEN ELECTRODE PADS ARE UNSUITABLE FOR USE BY DETECTING RELATIVE HUMIDITY

(75) Inventors: Kim J. Hansen, Renton, WA (US); Thomas A. Solosko, Issaquah, WA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 09/789,639

(22) Filed: Feb. 22, 2001

(65) Prior Publication Data

US 2002/0113606 A1 Aug. 22, 2002

(51) Int. Cl.$^7$ ............................................... G01R 27/26
(52) U.S. Cl. ..................... 324/689; 206/438; 206/459.1
(58) Field of Search ................................ 324/689, 696; 206/205, 524.1, 524.2, 524.4, 701; 427/2.11, 2.31; 422/50, 55, 56, 57, 58; 426/87, 88, 231, 232; 435/805, 810; 436/1; 73/73; 116/200, 206, 278; 340/601, 602, 693.5, 693.6

(56) References Cited

U.S. PATENT DOCUMENTS

| | | | | |
|---|---|---|---|---|
| 3,943,557 A | * | 3/1976 | Frazee et al. | 357/75 |
| 4,150,570 A | * | 4/1979 | Fuller | 73/335 |
| 4,990,284 A | * | 2/1991 | Lauterbach et al. | 252/408.1 |
| 5,080,099 A | * | 1/1992 | Way et al. | 128/640 |
| 5,165,947 A | * | 11/1992 | Colucci et al. | 426/41 |
| 5,674,275 A | * | 10/1997 | Tang et al. | 607/152 |
| 5,875,892 A | * | 3/1999 | Martin et al. | 206/459.1 |
| 5,975,288 A | * | 11/1999 | Crowder et al. | 206/205 |
| 5,984,102 A | * | 11/1999 | Tay | 206/701 |
| 6,157,306 A | * | 12/2000 | Mularoni | 340/602 |
| 6,209,717 B1 | * | 3/2001 | Flynn | 206/204 |
| 6,324,896 B1 | * | 12/2001 | Aoyagi et al. | 73/29.01 |

* cited by examiner

Primary Examiner—Safet Metjahic
Assistant Examiner—Etienne P LeRoux

(57) ABSTRACT

A sealed package for housing an electrical component. The package includes at least two package portions. Determining elements within the sealed package determine at least one parameter including at least one ambient condition within the package and/or an electrical function parameter of the component. An indicator is operatively connected to the determining elements to indicate the functionality of the component within the sealed package.

6 Claims, 2 Drawing Sheets

METHOD OF DETERMINING WHEN ELECTRODE PADS ARE UNSUITABLE FOR USE BY DETECTING RELATIVE HUMIDITY

BACKGROUND OF THE INVENTION

1. Field of the Invention

The present invention relates to a sealed package that permits verification of conditions within the package and/or functionality of components sealed within the package without unsealing the package. Also, the present invention relates to a method for determining conditions within the package and/or functionality of components sealed within the package without unsealing the package.

2. Description of the Prior Art

Many products are sealed in packages for various reasons. Examples of reasons for sealing products in a package can include maintaining sterility of the products, preventing contact of the products with air, and for protection during shipping, among others. For any one or more of these reasons, it may be desired to maintain a certain atmosphere within a sealed package. Along these lines, it may be desired to maintain temperature, gas composition, humidity and temperature, among other variables, within certain ranges.

Maintaining products at certain conditions may be preferable or necessary to maintain functionality of the products. Of course, once a package is opened, the conditions within the package are no longer the same as within the sealed package, unless the exact conditions within the package are known and duplicated in the external environment that the package is opened in. Also, over time conditions within a package can change, resulting in changes to the product(s) sealed within. If the conditions that a product is stored in affect its functionality, it may be desired to discard or refresh products that may no longer be functional due to storage conditions and/or the length of the storage period.

According to one particular example, it is typically desired to maintain products in a sterile environment. It may also be desirable and/or necessary to maintain medical products in a certain atmosphere to maintain the functionality or optimal functionality of the products. Opening a package that contains a medical device compromises the sterility of the device. Therefore, it can be particularly difficult to determine the status of a medical device since opening the package compromises the sterility of the device.

To ensure that medical devices in particular are suitable for use, a destruction policy may include discarding all devices with a certain age. This may be necessary due to the inability to know the qualities of a device. Such a destruction policy may result in discarding and thereby wasting viable devices.

For example, electrode pads may include a hydrogel that facilitates their operation. The shelf life of electrode pads is determined in part by the length of time it takes for enough water moisture to evaporate out of the hydrogel and escape the pads package. As moisture escapes, the electrical properties of the electrode pads may become increasingly compromised.

In one context, where electrode pads are utilized with a defibrillator, a very significant factor includes changes in small and large signal impedance values between a patient and a defibrillator. As the hydrogel dries out, the impedance values increase, making it more difficult to monitor a patient's electrical signals, obtain transthoracic impedance, and deliver energy into the body.

Water loss can affect the mechanical properties of the hydrogel as well. In some hydrogels, the loss of water causes the hydrogel to skin over or solidity, especially around the edges, which destroys the ability of the hydrogel to adhere to the skin. This partial or complete loss of adhesion can render an electrode useless since it cannot then create or maintain an effective contact with the skin. Thus, the drying of the electrode pad can prevent or attenuate receipt of electrocardiogram (ECG) signals by a defibrillator and can alter the delivery of defibrillation energy to the patient.

Additionally, poor or uneven contact of the electrode pad with a patient's skin may unduly concentrate energy transfer during defibrillation into areas that exhibit good skin contact. Higher than usual current densities that result from poor or uneven skin contact can cause skin burns. If the current is not delivered by the defibrillator to a patient in the manner that an electrode pad was designed for, the resulting treatment delivered to the patient may be altered.

To help ensure that electrode pads will be usable when opened, electrode manufacturers currently print an expiration date on each set of pads. The electrode pads are to be discarded no later than the expiration date. However, the expiration date typically is determined based upon studies of the hydrogel used on the pads, and the amount of water moisture that escapes the package over time under normal as well as strenuous conditions. A safety factor is added to give time for the electrode pads to be shipped from the supplier to an original equipment manufacturer (OEM), and then from the OEM to the customer. This helps to ensure that the electrode pads are always usable, barring any package damage, when removed from the package before the expiration date.

Calculating the expiration date of electrode pads or other components as described above is a conservative method of ensuring quality. However, as a result, the expiration date may arrive before the pads have actually expired. In fact, electrode pads may be usable for much longer than the expiration date, especially if they are kept at room temperature or in a high humidity environment.

While electrode pads or other components may naturally over time become nonfunctional, at other times an electrode package may be damaged in some way. For example, tiny punctures or slits in the package which may be too small to be seen by the casual observer or with the naked eye, or tears in the metal packaging layer caused by bonding the package, can allow water moisture to escape. Without noticing damage to the electrode pads' package, a customer typically will not replace electrode pads until the expiration date arrives, when in fact the hydrogel on those pads may be dry and unusable long before.

The above example only represents one particular example of an electrode pad of a particular use. Electrode pads for other uses may be similarly affected. Also, devices other than electrode pads may be affected by age and package conditions. Furthermore, factors other than humidity can affect the functionality of a device.

SUMMARY OF THE INVENTION

The present invention addresses problems related to ensuring operability of packaged devices. The present invention may be useful with a variety of products affected by a variety of conditions in their package. One advantage of the present invention is that the functionality of a device or component may be measured directly or indirectly while the device or component is still sealed in its package.

As such, the present invention relates to a sealed package for a component. The package includes at least two package portions. Determining elements within the sealed package permit determination of at least one parameter including at least one ambient condition within the package. An indicator operatively connected to the determining elements indicates the functionality of the component within the sealed package.

The present invention also relates to a method for determining functionality of a component in a sealed package. According to the method, at least one ambient condition within the package. It is then determined whether the parameter corresponds to an acceptable value at which the component functions. Next, it is indicated whether the parameter corresponds to an acceptable operational value for the component.

Still other objects and advantages of the present invention will become readily apparent by those skilled in the art from a review of the following detailed description. The detailed description shows and describes preferred embodiments of the invention, simply by way of illustration of the best mode contemplated of carrying out the present invention. As will be realized, the invention is capable of other and different embodiments and its several details are capable of modifications in various obvious respects, without departing from the invention. Accordingly, the drawings and description are illustrative in nature and not restrictive.

BRIEF DESCRIPTION OF THE DRAWINGS

Objects and advantages of the present invention will be more clearly understood when considered in conjunction with the accompanying drawings, in which.

DESCRIPTION OF THE PREFERRED EMBODIMENTS

Figure 1A:
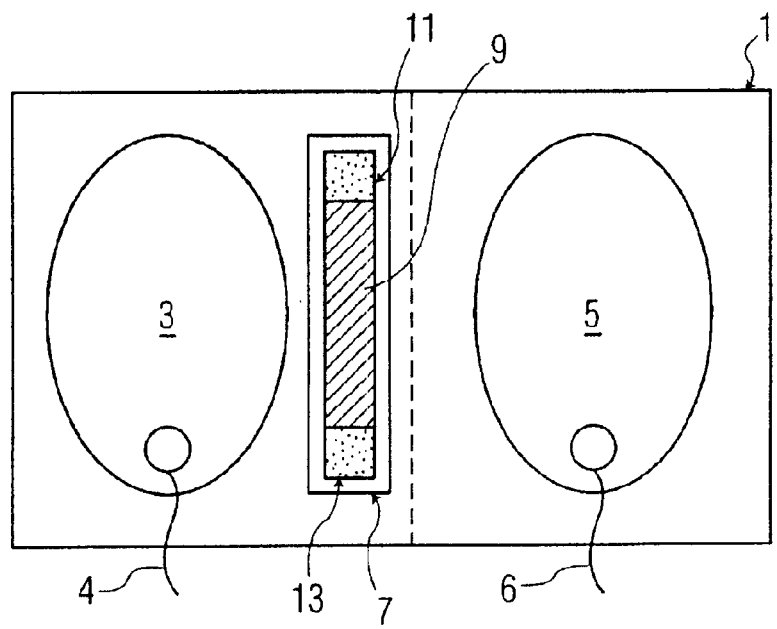
FIG. 1a represents an embodiment of a set of packaged electrodes on a release liner that includes a strip of moisture sensitive ink attached to the release liner according to the present invention.

As discussed above, storage conditions can affect the functionality of many devices. Whether temperature, humidity, environment or other factors are relevant, when sealed in a package, the functionality of a device typically cannot be known. Even out of a package, it may not be possible or easy to determine the operational status of a device. For example, whether an electrode pad has dried out too much may not be easy or possible to determine, particularly in a situation where the pad is urgently required and/or any testing equipment is not present. Factors other than humidity may be relevant to functionality of a device. Therefore, it may be desirable to measure factors other than humidity or to have a way to measure the functionality of a device.

The present invention addresses, among others, problems associated with drying out of hydrogel on electrode pads, regardless of the device that they are operatively connected to, to extrapolate the functionality of the pads. Although electrode pads are specifically mentioned here, the present invention may be applied to devices other than electrode pads and to conditions other than humidity that can affect operability of the devices.

With respect to determining electrical functionality of electrode pads, with preconnected electrodes, electrodes operatively connected electrically to fit a defibrillator before an emergency occurs, offer the possibility of testing the continuity of the electrical path from the defibrillator, through both electrode pads and back to the defibrillator. Several electrode continuity-testing schemes are in use.

A significant aspect of the schemes involves the manner in which electrical contact is made between the two electrodes. According to one scheme, a piece of metal foil is placed in contact with the hydrogel of both electrodes. The test current goes through the lead wire of one electrode, into the metal conductor, through the gel to this piece of metal foil. From the foil, the current travels through the gel of the second electrode, into its conductive layer, through its lead wires and back to the device.

A second method places the electrode pad hydrogels onto a common release liner with holes. The holes allow the gel of both electrodes to touch. In this way, the current travels from the device through one lead wire, into the electrode conductor, through the first gel, into the gel of the second electrode, through the conductive layer and lead wires of the second electrode and back to the device.

Both of the above-described methods have one thing in common, which is that the current is forced to travel through the hydrogel of the electrode pads. This is undesirable because each time current passes through the gel, tiny bubbles are formed which may decrease electrical performance of the electrode. As a result, the actual testing of the pads compromises their operability.

The present invention overcomes problems associated with methods and structures for testing, operability of electrode pads and monitoring conditions within a package. In one broad sense, the present invention provides a sealed package for a component. While the present invention may be useful with any component, as described herein, it was first developed for use with electrode pads. The present invention utilizes humidity as an indicator of functionality.

A package according to the present invention typically includes a package portion. More typically, the package includes at least two package portions that the component is sealed within. The package could include a pouch, rigid or semi-rigid member with a cover, or any other construction.

Elements permit the determination of at least one ambient condition within the package. The elements may be sealed within the package. At least one indicator indicates the at least one ambient condition within the package, thereby permitting the functionality of the component within the sealed package to be determined or inferred.

To permit the present invention to help determine the operability of components while still sealed in their containers, the indicator may be visible from outside the sealed package. This does not necessitate the indicator being arranged within the package. In fact, the indicator could lie outside the package and be operatively connected to elements within the package. In such an embodiment, the indicator would be visible from outside the sealed package. According to such embodiments, the elements to determine the ambient condition(s) within the package could also be arranged outside of the package. Such elements could include laser detectors and/or other detectors that permit the sensing of conditions within a package.

According to other embodiments, the indicator(s) is located within the sealed package. At least one transparent portion may be included in at least one of the package portions to permit the indicator(s) to be viewed. In addition to its location, the nature of the indicator may also change.

As stated above, humidity is one ambient condition within a package that is particularly relevant to electrode pads. The present invention can measure the relative humidity condition (% RH) inside the sealed package. The % RH reading may be displayed to a user in a variety of manners, depending upon the embodiment. One embodiment can display to the user either a "good/not good" indication. Another embodiment can make the condition of the pads clearly visible to the user. An objective of the present invention is to alert a user when electrode pads of any other device have lost enough moisture that their electrical and/or mechanical properties have deteriorated below the specified limits.

Not only can hydrogels dry out, they can gain too much moisture. This is particularly true if the hydrogel or the package containing the hydrogel is stored in an environment with a high relative humidity. As a hydrogel gains moisture, it can swell and loose adhesive properties. As a result, electrode pads may become unusable.

To detect humidity and, thus, to extrapolate to the moisture content of the hydrogel in the pad, the present invention may include humidity sensitive ink in and/or on the package. The humidity sensitive ink may be visible regardless of the humidity and change appearance with changing humidity. In embodiments of the present invention that include humidity sensitive ink, the determining means can be considered the same as the indicating means.

If another parameter(s) is of importance, the ink could change with changes in the other parameter(s). Along these lines, temperature could be of issue and the ink could become visible to indicate that the storage temperature has been too high or too low. Additionally, if it were important that an item were stored in a certain gaseous environment, the ink could change with exposure to certain gasses, such as oxygen.

In an example where humidity is the parameter of issue, humidity sensitive ink change color with changes in humidity may be utilized. A reference color chart can permit a user to determine the humidity within the package. The reference chart may or may not be enclosed within the package.

Alternatively, at least some portion of the humidity sensitive ink may become visible with changes in humidity. For example, as the humidity becomes too low to ensure a functional electrode pad, the ink could become visible. Along these lines, the ink could appear as to print text or symbols. For example, the message "expired", "pads-ok" or another message could appear, depending upon the humidity. The ink could also appear if humidity becomes too high. One benefit of such an embodiment is that it does not require comparison to a reference color spot while still indicating a need to replace the pads. According to one embodiment, the humidity sensitive ink is printed on a background having a color that is the same color as the ink when conditions in a package are acceptable. When the humidity within the package deviates from acceptable levels, the humidity indicator ink will change color, thereby standing out from its background, and become visible.

One inexpensive embodiment of the present invention includes a two-piece package having one transparent portion. According to one embodiment, the package can be one-half metal foil. The other half can be clear or transparent. For example, the clear half can be a clear non-foil laminate. One example of such a laminate is an Aclar laminate, produced by Honeywell. The clear or transparent portion may also be formed from Topas®, which is produced by Ticona, or partially metallic clear film like anti-static film often used to package static-sensitive semiconductor components. The clear or transparent package portion can permit a user to see the humidity indicator inside the package.

The humidity sensitive ink may be included in a package on a humidity indicator card. Humidial Corporation produces an embodiment of such a card that is printed with inks that change color with humidity. Such inks typically are cobalt chloride based. As described above, the cards can be designed with a reference bar, so that when the color of the indicator spot turns the same color as the reference bar, a user knows that the electrode pads or other humidity sensitive items have lost too much moisture and are no longer usable. The card may be adhered to the transparent or clear portion of the package with adhesive to hold the humidity indicator card to the inside surface of the clear packaging layer. The card may also be adhered to a component of the electrode assembly such as the release liner.

According to one embodiment that includes a card printed with humidity sensitive ink, humidity indicator ink turns from light pink, in humid conditions, to dark blue, in dry conditions. The relative humidity inside the package may be kept fairly constant by the hydrogel at between about 50% and about 70% RH, depending on the gel. As the gel dries out due to water moisture slowly escaping from the package, the hydrogel cannot continue to give the necessary amount of moisture to the inside of the package to keep the package at a constant and acceptable level to maintain the hydrogel in the desired functional state. When this happens, the relative humidity inside the package decreases causing the color of the indicator ink to darken and turn bluer.

If 40% RH is the level at which the gel's electro/mechanical properties deteriorate beyond acceptable limits, the reference bar included on the humidity indicator card next to the indicator dot, will show the shade of blue that the ink will turn when a level of 40% RH is reached inside the package. Regardless of the particular target humidity level, to determine if a set of pads is still usable, a user, with this embodiment will compare the color of the ink dot to the reference color. If the ink dot is lighter or pinker, the electrode pads are usable. On the other hand, if the ink dot is as dark or darker blue than the reference color, the pads may be too dry and should be discarded. Of course, the critical level of humidity can change, as can the color change of the ink, as well as the relevant parameter.

An interesting aspect of hydrogels is that they can absorb as well as give off moisture. Along these lines, relative humidity testing of gel indicates that relative humidity levels inside packages of hydrogel do increase when the % RH of the outside environment is high, such as on the order of about 80% to about 100% RH. Since hydrogels can absorb moisture as well as give off moisture, an increase in the amount of water vapor inside the package due to moisture entering the package from the environment external to the package can have a limited "healing" effect on dry electrodes. As a result, the ink dot can change color from a darker blue to a lighter blue or pink. This change could indicate that the electrodes are again acceptable for use.

The humidity indicator can be used in the "healing" of the pads, in other words, to help recondition dry electrode pads. For example, unopened packages of dry electrode pads could be placed in an environmental chamber at or above room temperature and about 90% to about 100% RH. The humidity indicators inside each package could indicate when the RH level inside each package has returned to normal levels. Depending on the type of package, this might take an extended period of time. For example, the healing could take from about several hours to several weeks. However, without the humidity indicators, each package of electrodes would have to be opened so that the electrodes could be confidently reconditioned to an acceptable level. If the pads are sterile, opening the package will compromise the sterility of the electrode pads.

As referred to above, when a hydrogel gains too much moisture, it can swell and lose its adhesive properties. If the electrode packages are continuously stored in a high % RH environment the package may gain enough moisture to cause the hydrogel on the electrodes to swell and become unusable. The present invention can help to identify probable non-functional electrode pads in such situations as well. Along these lines, when the hydrogel swells with water moisture, it can no longer keep the % RH inside the package at normal levels. Using the same indicator dot described above, but adding a light blue or pink reference bar above the dot, the user will know when the inside of the package has reached an unacceptably high % RH level. This will tell the user if the electrode pads have become unusable due to excess moisture gain.

As with the dry-environment situation, having the humidity indicator inside the package can be especially useful if the package has been damaged in some way and is permitting excess moisture to reach the pads or causing excess moisture loss from the pads. Having two reference bars, one at an upper % RH limit and one at a lower % RH limit, enables the user to confidently ascertain if the electrodes are within their operating specifications.

Rather than being printed on a card that is placed in a package, humidity sensitive ink could be printed directly on a clear, transparent or translucent portion of a package. As the ink changes with changing humidity, it would be visible to a user. The ink could also be printed on the electrode release liner(s) or on the electrode pads themselves.

FIG. 1a illustrates an embodiment of the present invention that includes a strip 7 of moisture sensitive ink 9 attached to the release liner 1 that the electrode pads 3 and 5 are attached to. Leads 4 and 6 extend from electrode pads 3 and 5, respectively. The moisture sensitive ink could be printed directly on the release liner or on a separate element, such as a piece of paper, attached to the release liner, as in the embodiment shown in FIG. 1a. The strip 7 on which the ink 9 is printed includes reference regions 11 and 13, which provide a reference of the color of the ink when humidity is too high and too low, respectively. These reference colors could be positioned on the side(s) of the strip 7 or elsewhere rather than on each end as shown in FIG. 1a. Additionally, the strip could include just one reference color of the humidity sensitive ink when the humidity falls too low, for example.

Figure 1B:
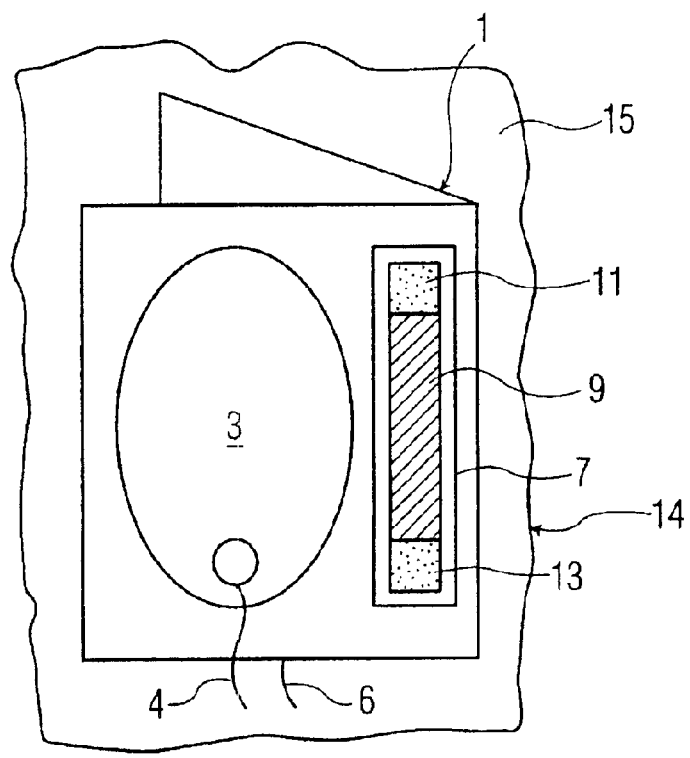
FIG. 1b represents the embodiment of the present invention shown in FIG. 1 in a package that includes a clear front portion that permits the ink to be viewed with the package sealed.

FIG. 1b shows the embodiment illustrated in FIG. 1a enclosed in a package 14. The package includes a transparent portion 15 that permits viewing of the humidity sensitive ink and, thereby, the humidity within the package.

Rather than including humidity sensitive ink, a package according to the present invention could include an electronic or mechanical humidity sensor. The sensor could be placed inside a package. An indicator for displaying relative humidity could be placed inside the package to be viewed by a user. Alternatively, the package could include a receptacle into which the indicator could plug, thereby connecting the indicator with the sensor. The indicator in embodiments that include a sensor could include a meter or display, such as any light-producing element.

According to one embodiment, a package is sealed around a lead wire connecting a humidity sensor to a defibrillator. The sensor could alert the defibrillator via electronic communication means when the % RH inside the package has become too low or too high. Examples of communication means can include contact/no contact or/and establishing and monitoring an analog representation of the humidity within the package. The defibrillator could in turn notify the user that it was time to replace the pads. Examples of devices other than defibrillators that the present invention could be utilized with include an electroencephalograph or an electrocardiograph. Although, the present invention may be employed with any device as desired.

An embodiment of the present invention that utilizes a humidity sensor can have one or more of the following or other advantages over embodiments that include humidity sensitive ink: 1) a humidity sensor allows the electrodes to be packaged in a package made of an all-foil or other non-clear material; non-clear materials can be less expensive than clear materials, and can provide a better moisture vapor barrier; 2) embodiments that include a humidity sensor can permit external monitoring of the environment inside the electrode package and alert a user when unacceptable levels are reached; and 3) embodiments that include a humidity sensor can eliminate user judgement of color, and gives color-blind users feedback on the state of electrodes.

Another embodiment of the present invention includes an electronic humidity indicator packaged inside a package with the electrodes and electrode pads. This indicator could illuminate a light or give a reading when the % RH inside a package becomes unacceptable. However, this embodiment would require a package that includes at least a portion that is clear, transparent or translucent. An embodiment that includes an indicator inside the package could enable color-blind users to determine the state of electrodes, and would not rely upon an external device, such as a defibrillator, to interpret the messages from a humidity sensor.

Figure 2:
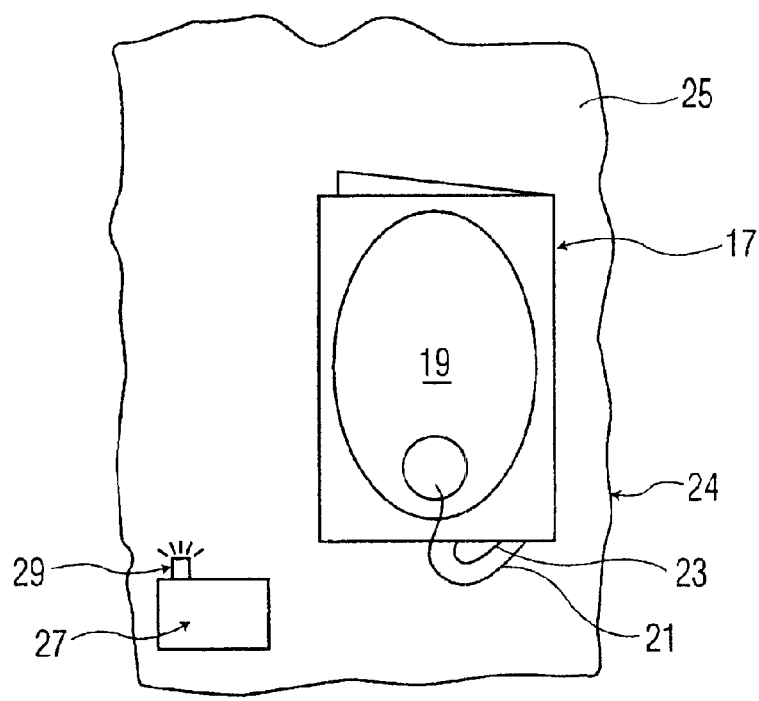
FIG. 2 represents an embodiment of a set of packaged electrodes on a release liner in a package with a transparent portion and in which a humidity sensor or detector is included according to the present invention.
Figure 3:
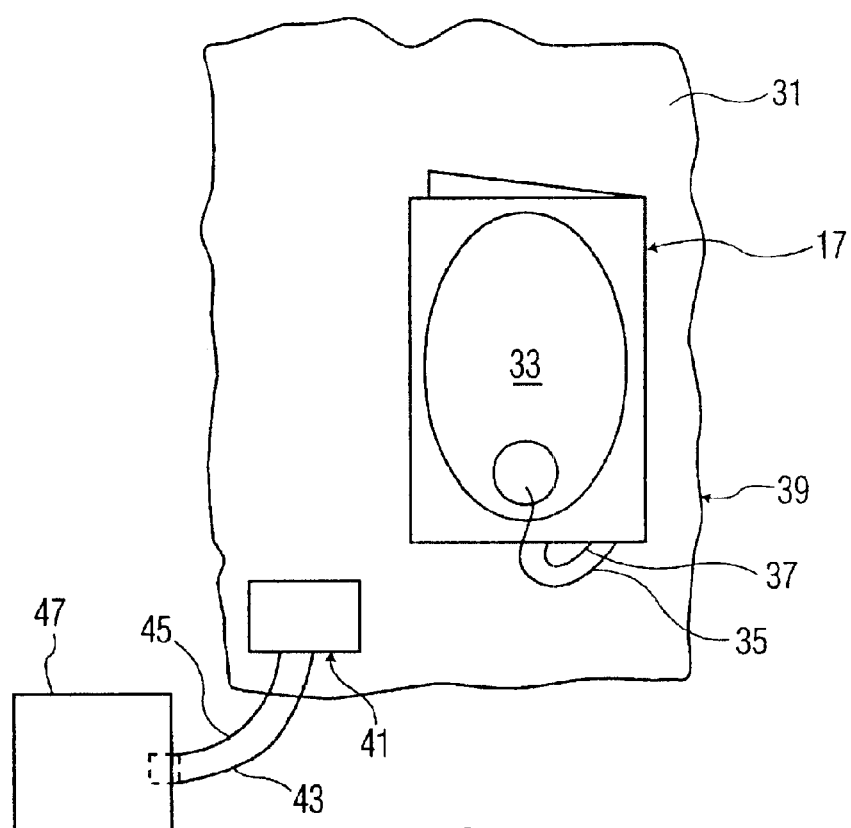
FIG. 3 represents an embodiment of the present invention that includes a packaged set of electrodes on a release liner and a humidity sensor or detector sealed inside the package with lead wire(s) extending from the sensor through the package seal.

FIGS. 2 and 3 illustrate embodiments of the present invention that include humidity detectors rather than humidity sensitive ink. Along these lines, FIG. 2 shows an embodiment of the present invention that includes electrodes, only one of which electrode 19 is shown, on a release liner 17. Leads 21 and 23 extend from the electrodes. The electrodes are packaged in a package 24 that includes a transparent member 25.

A humidity sensor 27 is also located inside the embodiment of the package shown in FIG. 2. The humidity sensor includes an indicator for indicating humidity or when humidity has a certain value. Along these lines, the indicator could indicate when humidity is too high and/or too low. In the embodiment shown in FIG. 2, the humidity detector illuminates a light 29 if the humidity goes above or below a certain range.

Rather than include an indicator, the humidity sensor may include leads that permit attachment of an indicator to the humidity detector. FIG. 3 illustrates such an embodiment of the present invention. The embodiment shown in FIG. 3 includes electrodes, only one of which electrode 33 is shown, on a release liner 31. Leads 35 and 37 extend from the electrodes. The electrodes are packaged in a package that includes a transparent member 39.

In the embodiment shown in FIG. 3, a detector 41, such as a humidity detector or other detector, is also located in the package. A pair of leads 43 and 45 extend from the detector 41. The package is sealed about the leads 43 and 45 to ensure that the interior of the package is not compromised. The leads may be attached to an instrument 47 external to the package for indicating whatever parameter the detector detects. The external instrument, such as a defibrillator or an indicator, could display the relative humidity level inside the package, and may equate this to the fitness-for-use condition of the pads. The external instrument could also detect, monitor and/or measure temperature, oxygen concentration, or concentration of a pre-determined dopant material released inside the package, or any other parameter.

In the case of electrodes for a defibrillator it is necessary that pads be functional. That is why a very conservative expiration date is associated with such pads. As a result, many viable pads are discarded. This embodiment, as well as others, provides a package and method for determining whether pads are viable while still sealed in a package.

With respect to embodiments that relate to relative humidity within a sealed package, a purpose of the present invention is to alert a user when the % RH level inside the electrode package becomes too low or too high, indicating that the electrodes will not perform to their specifications. This ultimately is intended to increase the shelf life of the electrodes, since a hard and fast expiration date would not be necessary. The present invention can alert users of damaged pad packages.

However, the shelf life of some gels depends on properties other than moisture loss. For example some gels corrode the conductive layers that they contact in thus cases, it would be faulty to use the % RH levels as the only indication of pad health and usability. Other tests, such as electrical testing, are a better alternative in this case. In some cases, the electrodes may need to be operatively connected to the instrument or a separate measurement device.

This present invention provides a versatile method of determining when electrode pads in particular have expired. It can be used with either pre-connected or non-preconnected electrodes. It can be used with defibrillator electrodes or ECG/EKG electrodes. Different embodiments can address different methods of measuring and indication moisture related electrode deterioration. In some cases, more than one embodiment may be utilized to gauge and indicate the usability of electrode pads or other devices in a sealed package.

In certain embodiments, the present invention can also permit remote determination of the status of the sealed package and/or the component(s) sealed therein. For example, once the humidity or functional status of the component(s) sealed therein is determined, it could be transmitted via wired or wireless communication means to a location remote from the package. A notification could then be produced that replacement of the component is required. In the case of defibrillator electrode pads, an embodiment with remote notification could permit electrode pads to be changed to be sure that the defibrillator will function as necessary. This could be particularly important for defibrillators in public places meant to provide defibrillators immediately available on an emergency basis.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed:

1. A sealed package for housing an electrical component, the package comprising:

determining means within the sealed package for determining at least one parameter including at least one ambient condition within the sealed package; and an indicator operatively connected to the determining means to indicate the functionality of the component within the sealed package without having to unseal the package, wherein the parameter comprises humidity and the determining means and indicator are integral and comprise a humidity detector that includes humidity sensitive ink, wherein said ink changes color as the humidity level changes and further wherein the indicator further comprises at least one reference region that indicates ink color corresponding to at least one of acceptable and unacceptable humidity levels.

2. The package according to claim 1, wherein the indicator is visible form outside of the sealed package and at least a portion of the package is at least partially transparent.

3. A sealed package for housing an electrical component, the package comprising:

determining means within the sealed package for determining at least one parameter including at least one ambient condition within the sealed package; and an indicator operatively connected to the determining means to indicate the functionality of the component within the sealed package without having to unseal the package, wherein the parameter comprises humidity and the determining means comprises a humidity sensor, and further wherein the humidity sensor further includes at least one lead wire that extends from the sealed package for operatively connecting to an apparatus external to the package.

4. The package according to claim 3, wherein the component includes electrodes for contacting a patient's skin, the electrodes comprising a hydrogel layer, wherein the external apparatus comprises a device that the electrodes are to be operatively connected to, the indicator being included with the device, and wherein the sensor transmits the humidity to the device via the at least one lead wire.

5. The package according to claim 4, wherein the device comprises one of a defibrillator, an electroencephalograph or an electrocardiograph.

6. A method for determining functionality of a component in a sealed package, the method comprising:

determining at least one parameter comprising at least one ambient condition within the sealed package without having to unseal the package;

determining whether the parameter corresponds to an acceptable value at which the component functions; and indicating whether the parameter corresponds to an acceptable operational value for the component, wherein determining the at least one parameter comprises operatively connecting the component to a device external to the package, and further wherein the at least one ambient condition comprises humidity.

* * * * *